United States Patent [19]

Mookherjee et al.

[11] 4,092,333
[45] May 30, 1978

[54] 2-ACYL-5-SUBSTITUTED THIATETRAHYDROFURAN-4-ONES

[75] Inventors: Braja Dulal Mookherjee, Holmdel; William J. Evers, Middletown, both of N.J.; Alfred E. Goossens, New York, N.Y.

[73] Assignee: International Flavors & Fragrances Inc., New York, N.Y.

[21] Appl. No.: 819,888

[22] Filed: Jul. 28, 1977

[51] Int. Cl.² ............... C07D 307/32; C07D 307/64
[52] U.S. Cl. ..................... 260/347.2; 131/17 R; 252/89 R; 252/132; 252/522; 426/535
[58] Field of Search .................. 260/347.2; 426/535

[56] References Cited
U.S. PATENT DOCUMENTS 3,985,907  10/1976  Evers et al. .................. 426/535

*Primary Examiner*—Richard L. Raymond
*Attorney, Agent, or Firm*—Arthur L. Liberman; Franklin D. Wolffe

[57] ABSTRACT

Described are 2-acyl-5-substituted thiatetrahydrofuran-4-ones having the generic structure:

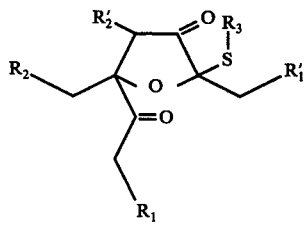

wherein $R_1$, $R_2$, $R_1'$ and $R_2'$ are the same or different and each represents hydrogen or methyl and wherein $R_3$ represents one of $C_1$–$C_9$ alkyl, benzyl, phenyl, substituted or unsubstituted allyl having the structure:

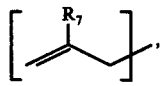

substituted or unsubstituted 3-furyl having the structure:

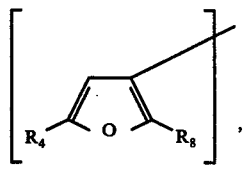

(wherein $R_4$ and $R_8$ are the same or different and each represents hydrogen or methyl) hydroxy alkyl, oxoalkyl, hydroxycycloalkyl or oxocycloalkyl having the structure:

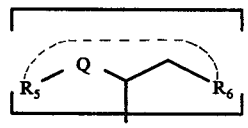

(wherein $R_5$ and $R_6$, taken separately, represent hydrogen or $C_1$–$C_3$ alkyl or $R_5$ and $R_6$, taken together, complete a cycloalkyl group and wherein Q is one of the moieties:

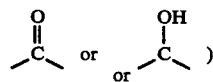

The 2-acyl-5-substituted thiatetrahydrofuran-4-ones of our invention have organoleptic properties which make them useful for augmenting or enhancing the aroma or flavor of foodstuffs, tobaccos and the aroma of perfumes and perfumed articles.

2 Claims, No Drawings

2-ACYL-5-SUBSTITUTED THIATETRAHYDROFURAN-4-ONES

BACKGROUND OF THE INVENTION

The present invention relates to 2-acyl-5-substituted thiatetrahydrofuran-4-ones produced by the novel process of our invention and novel compositions using one or more of such 2-acyl-5-substituted thiatetrahydrofuran-4-ones or "cis" or "trans" isomers thereof to alter, modify, augment or enhance the flavor and/or aroma of consumable materials or impart flavor and/or aroma to such consumable materials.

There has been considerable work performed relating to substances which can be used to impart (modify, augment or enhance) flavors to (or in) various consumable materials. These substances are used to diminish the use of natural products, some of which may be in short supply and to provide more uniform properties in the finished product. Coffee-like, roasted, cocoa-like, caramel-like, licorice and roasted almond aroma and flavor characteristics are particularly desirable for many uses in foodstuff flavors, chewing gum flavors, toothpaste flavors and medicinal product flavors. Sweet, caramel/coffee aromas and flavors prior to smoking and sweet, caramel/coffee, nutty/pyrazine and roasted nutty aroma and taste characteristics on smoking are particularly desirable in tobaccos as well as tobacco flavoring compositions and in tobacco substitutes and flavoring compositions for such tobacco substitutes.

When one mole of diacetyl is reacted with one mole of furfuryl mercaptan, a coffee flavored reaction product is produced which has been found to contain a small percentage (about 10% by weight) of 5-acetyl-2-(furfurylthio)dihydro-2,5-dimethyl-3-[2H]furanone with one mole of the "cis"-"trans" isomers in a ratio to the other of the "cis"-"trans" isomers of about 2:1. The process for preparing such a reaction product (without describing the constituents of the products) is set forth in Swiss Pat. No. 128,720 published on Nov. 16, 1928. It is stated in the Example at Column 2 on page 1 thereof that when one mixes furfuryl-2-mercaptan and diacetyl, the product (alpha-oxy-alpha-acetylethyl)furfuryl-2-sulfide is produced.

U.S. Pat. No. 1,696,419 issued on Dec. 25, 1928 (Title: "Method of Producing Artificial Coffee Aroma") discloses the production of a coffee flavor using:

"One part of diacetyl, four parts of acetyl propionyl, four parts of methyl ethyl acetaldehyde, three parts of acetaldehyde, two parts of alpha methyl furfural, one part of furfural, three parts of pyridine, two parts of isovaleric acid, one part of phenol, one part of isoeugenol, 0.5 parts of guiacol, 0.5 parts of alpha methyl cyclopentenolone, 0.6 parts of methyl mercaptan, 0.3 parts of furfuryl mercaptan, 0.3 parts of n-octyl alcohol and 0.4 parts of thioguiacol"

at page 3, column 1, lines 29–39.

No member of the genus of compounds having the structure:

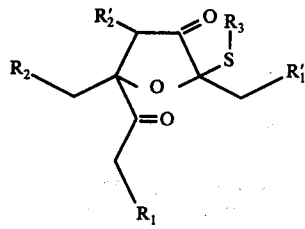

(wherein $R_1$, $R_2$, $R_1'$, $R_2'$ and $R_3$ are defined above) is indicated to be produced as a result of admixing at higher temperatures the foregoing ingredients.

Canadian Pat. No. 1,002,383 issued on Dec. 28, 1976 discloses the preparation of a popcorn-type flavor by reacting glyoxal (an alpha, beta-dicarbonyl compound) with a "sulfide source" at elevated temperatures. The resulting material is indicated to have advantageous properties over reaction products of "sulfide sources" with such materials as 2,3-pentane dione, which is indicated on page 8 to give rise to a product having a "burnt character" when it is reacted with a "sulfide source". Organic "sulfide sources" are also mentioned in Canadian Pat. No. 1,002,383, but are only exemplified by 1-cysteine.

Thus, nothing in the prior art discloses either explicitly or implicitly any member of the genus of the compounds having the structure:

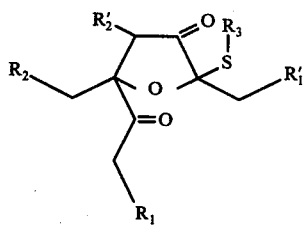

wherein $R_1$, $R_2$, $R_1'$ and $R_2'$ are the same or different and each represents hydrogen or methyl and wherein $R_3$ represents one of $C_1$–$C_9$ alkyl, benzyl, phenyl, substituted or unsubstituted allyl having the structure:

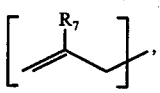

substituted or unsubstituted 3-furyl having the structure:

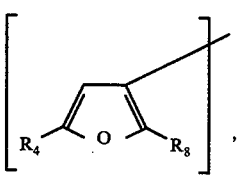

(wherein $R_4$ and $R_8$ are the same or different and each represents hydrogen or methyl), hydroxyalkyl, oxoalkyl, hydroxycycloalkyl or oxocycloalkyl having the structure:

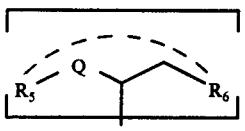

(wherein $R_5$ and $R_6$, taken separately, represents hydrogen or $C_1$-$C_3$ alkyl or $R_5$ and $R_6$, taken together, complete a cycloalkyl group) and wherein Q is one of the moieties:

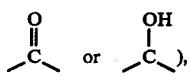

prepared according to the process of dimerizing one or more alpha, beta-alkane dione(s) to form one or more alpha, beta-alkane dione dimer(s) having the structure:

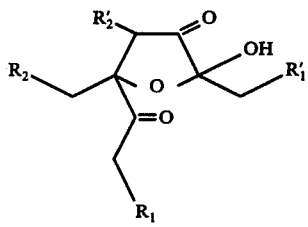

and reacting the said alkane dione dimer(s) in acidic medium and in the presence of a solvent with a mercaptan having the structure:

$R_3SH$

THE INVENTION

It has now been discovered that novel solid and liquid foodstuff, chewing gum, medicinal product and toothpaste compositions and flavoring compositions therefor having coffee-like and/or roasted and/or caramel-like and/or licorice-like and/or roasted almond aroma and flavor characteristics; novel tobacco and tobacco flavoring compositions as well as substitute tobacco and substitute tobacco flavoring compositions having sweet and/or caramel/coffee and/or nutty and/or roasted aromas and tastes prior to and on smoking and perfumery compositions and perfumed articles having pleasant woody aromas may be provided by the utilization of one or more 2-acyl-5-substituted thiatetrahydrofuran-4-ones (either "cis" or "trans" isomers or mixtures of "cis" and "trans" isomers) having the generic formula:

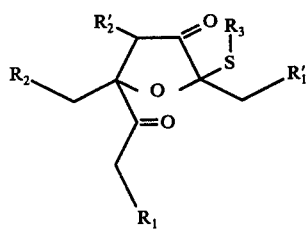

wherein $R_1$, $R_2$, $R_1'$ and $R_2'$ are the same or different and each represents hydrogen or methyl and wherein $R_3$ represents one of $C_1$-$C_9$ alkyl, benzyl, phenyl, substituted or unsubstituted allyl having the structure:

(wherein $R_7$ is hydrogen or methyl) substituted or unsubstituted 3-furyl having the structure:

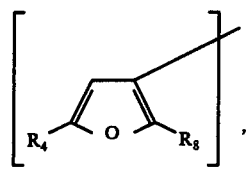

(wherein $R_4$ and $R_8$ are the same or different and each represents hydrogen or methyl), hydroxyalkyl, oxoalkyl, hydroxycycloalkyl or oxocycloalkyl having the structure:

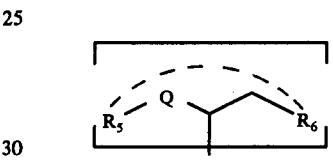

(wherein $R_5$ and $R_6$, taken separately, represent hydrogen or $C_1$-$C_3$ alkyl or $R_5$ and $R_6$, taken together, complete a cycloalkyl group and wherein Q is one of the moieties:

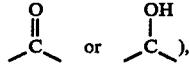

prepared according to the process of dimerizing one or more alpha, beta-alkane dione(s) to form one or more alpha, beta-alkane dione dimer(s) defined by the structure:

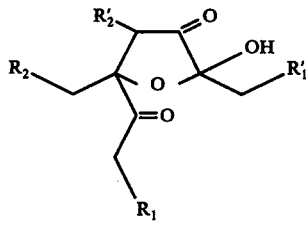

and reacting the said alkane dione dimer(s) in acidic medium and in the presence of a solvent with a mercaptan having the structure:

$R_3SH$ in foodstuffs, chewing gums, toothpastes, medicinal products, tobaccos, tobacco substitutes, smoking tobacco articles, chewing tobacco and perfumes and perfumed articles.

The 2-acyl-5-substituted thiatetrahydrofuran-4-ones useful as indicated supra, may be produced preferably by means of a process whereby one or more dimers of one or more $C_4$–$C_6$ alpha, beta-diketones is reacted with an organic mercaptan.

Thus, the process of our invention for producing 2-acyl-5-substituted thiatetrahydrofuran-4-ones having the structure:

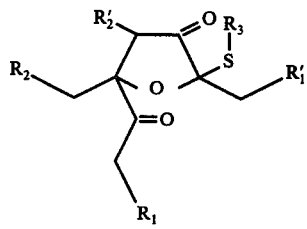

comprises reacting one or more dimers of $C_4$–$C_6$ alpha, beta-diketone(s) which dimer(s) are defined by the structure:

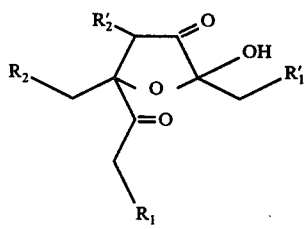

with a mercaptan having the formula:

$R_3SH$ in the presence of an acid catalyst, preferably a mineral acid catalyst such as hydrochloric acid, phosphoric acid, paratoluene sulfonic acid or sulfuric acid. The $C_4$–$C_6$ alpha, beta diketone dimer substance can be a mixture of dimers or a substantially pure dimer, which can be produced by reacting a particular alpha, beta-diketone with itself or with a second alpha, beta-diketone. Thus, in the case of particular dimers having the generic structure:

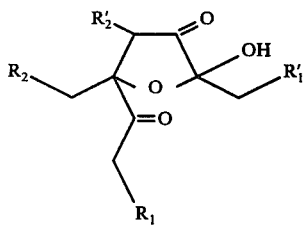

wherein $R_1$, $R_2$, $R_1'$ and $R_2'$ are the same or different and each represents hydrogen or methyl, such a dimer is formed using at least one $C_4$–$C_6$ alpha, beta-diketone defined by the structure:

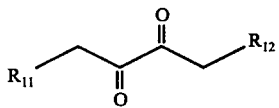

wherein $R_{11}$ and $R_{12}$ are the same or different; that is, either both represent hydrogen or both represent methyl or one of $R_{11}$ or $R_{12}$ is hydrogen and the other of $R_{11}$ or $R_{12}$ is methyl. In the case of using one alpha, beta-diketone for dimerization, in the event that one of $R_{11}$ or $R_{12}$ is hydrogen, and the other of $R_{11}$ or $R_{12}$ is methyl, a mixture of dimers would be formed as a result of the dimerization reaction wherein one of $R_1$ or $R_2$ is hydrogen and the other of $R_1$ or $R_2$ is methyl and, by the same token, one of $R_1'$ or $R_2'$ is hydrogen and the other of $R_1'$ or $R_2'$ is methyl. Further, insofar as the dimerization reaction of two different $C_4$–$C_6$ alpha, beta-diketones is concerned (the reaction taking place in the presence of a basic material such as sodium hydroxide, potassium hydroxide, sodium carbonate and potassium carbonate) each of the diketones individually will dimerize and the different diketones will also dimerize with one another; thereby forming a mixture of sixteen isomers and homologues, each isomer and each "homologue" being in both a "cis" and a "trans" form.

The aforementioned reaction sequence is set forth in a generic manner below:

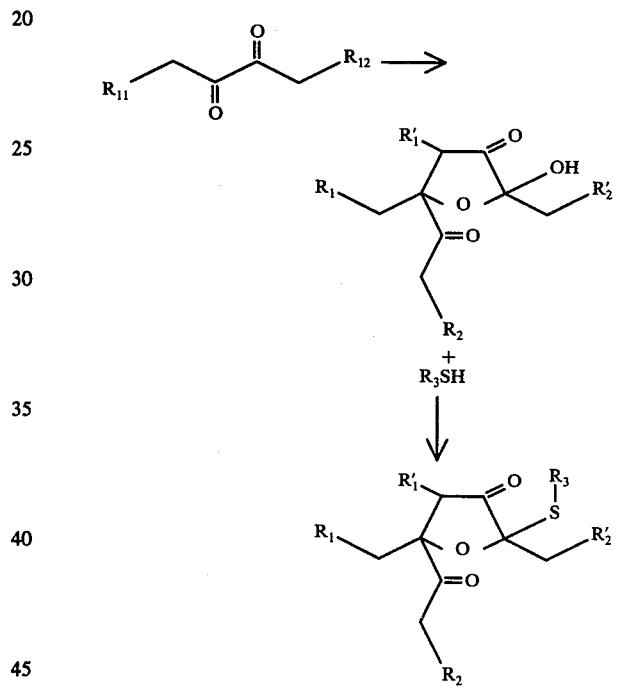

More specifically, this sequence is exemplified in accordance with the following reaction sequences:

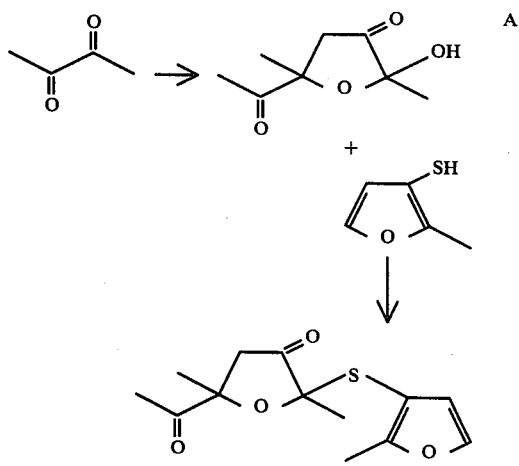

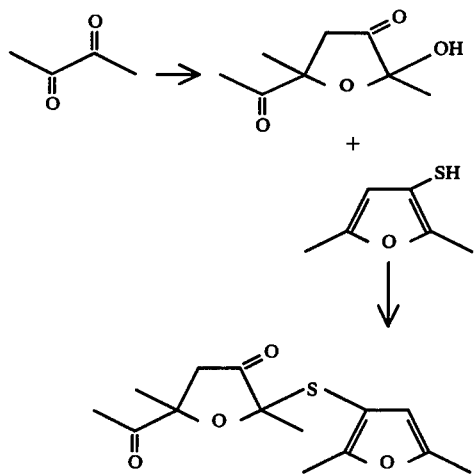
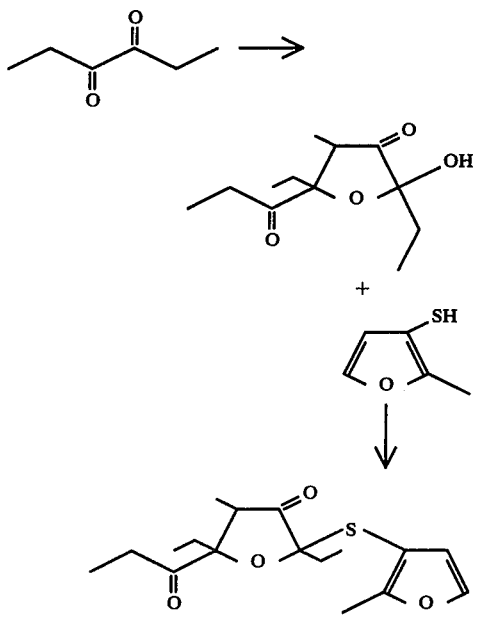
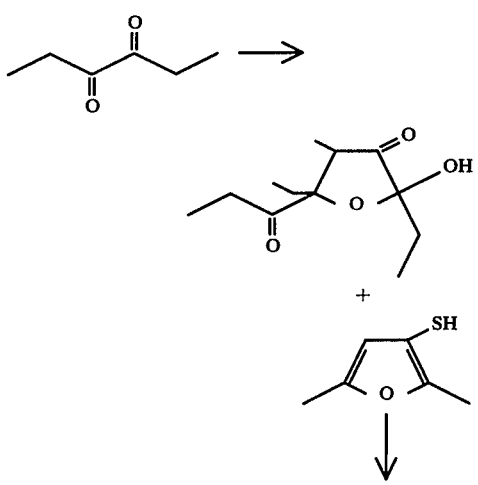
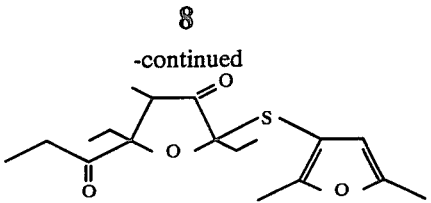

-continued

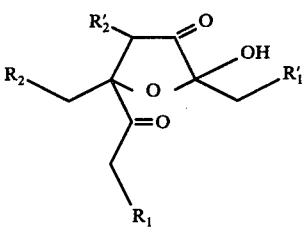

Insofar as the aforementioned sequences are concerned wherein one or more $C_4$-$C_6$ alpha, beta-alkanediones is reacted to form one or more "dimer(s)" having the structure:

the said dimer(s) is (are) prepared by methods well known in the art (e.g. dimerization of the $C_4$-$C_6$ alpha, beta-alkanedione in the presence of base). The reaction of the dimer(s) with the mercaptan ($R_3SH$) preferably takes place in the presence of a solvent at temperatures in the range of from about 40° up to about 100° C depending upon the solvents used and the time of reaction used. Preferably the solvent used is one wherein the reflux temperature of the reaction mass will be at temperatures of between 40° and 100° C such as, for example, tetrahydrofuran. The pressure of reaction is preferably and most conveniently about one atmosphere, however, pressures of reaction of greater than one atmosphere or less than one atmosphere may be used without detrimentally affecting the yield of desired product. In order to avoid problems relating to the recovery of excess reactants it is preferable to use a mole ratio of $C_4$-$C_6$ alpha, beta-alkanedione dimer: mercaptan ($R_3SH$) of 1:1 although either of the reactants may be used in excess without detrimentally affecting the yield of reaction.

One or more of the 2-acyl-5-substituted thiatetrahydrofuran-4-ones of our invention is capable of supplying and/or potentiating certain flavor and aroma notes usually lacking in many coffee, caramel, roasted nut and licorice flavors as well as tobacco flavors heretofore provided.

When the 2-acyl-5-substituted thiatetrahydrofuran-4-ones of our invention are used as food flavor adjuvants the nature of the co-ingredients included with each of the said 2-acyl-5-substituted thiatetrahydrofuran-4-ones in formulating the product composition will also serve to alter or augment the organoleptic characteristics of the ultimate foodstuff treated therewith.

As used herein in regard to foodstuff flavors and chewing gum flavors and medicinal product flavors, the terms "alter", "modify" and "augment" in their various forms mean "supplying or imparting flavor character or notes to otherwise bland, relatively tasteless substances or augmenting the existing flavor characteristics where a natural flavor is deficient in some regard or where a specific flavor composition containing several ingredients some of which may be natural, is deficient in some regard or supplementing the existing flavor impression to modify its quality, character or taste".

The term "enhance" is used herein to mean the intensification of a flavor aroma characteristic or note without the modification of the quality thereof. Thus, "enhancement" of a flavor or aroma means that the enhancement agent does not add any additional flavor note.

As used herein the term "foodstuff" includes both solids and liquids which are ingestible materials which usually do, but need not, have nutritional value. Thus, foodstuffs include soups, convenience foods, beverages, dairy products, candies, vegetables, cereals, soft drinks, snacks and the like and in addition, intended herein to mean pet foods.

As used herein the term "medicinal product" includes both solids and liquids which are ingestible non-toxic materials which have medicinal value such as cough syrups, cough drops, aspirin, vitamins, lozenges and chewable medicinal tablets.

The term "chewing gum" is intended to mean the composition which comprises a substantially water-insoluble, chewable plastic gum base such as chicle, or substitutes therefor, including jelutong, guttakay, rubber or certain comestible natural or synthetic resins or waxes. Incorporated with the gum base in admixture herewith may be plasticizers or softening agents, e.g., glycerine; and a flavoring composition which incorporates one or more of the 2-acyl-5-substituted thiatetrahydrofuran-4-ones of our invention, and, in addition, sweetening agents which may be sugars, including sucrose or dextrose and/or artificial sweeteners such as cyclamates or saccharin. Other optional ingredients may also be present.

Suitable substances for use herein as co-ingredients or "flavoring adjuvants" are well known in the art for such use, being extensively described in the relevant literature. It is a requirement that any such material be "ingestibly" acceptable unless non-toxic and otherwise non-deleterious particularly from an organoleptic standpoint whereby the ultimate flavor and/or aroma of the consumable material used is not caused to have unacceptable aroma and taste nuances.

Those materials which, in general, may be characterized as "flavoring adjuvants" comprise broadly vehicles, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include:
(I) Insofar as coffee flavors are concerned:
Hydrogen sulfide;
Formaldehyde;
Formic Acid;
Methanol;
Methyl mercaptan;
Carbon disulfide;
Acetaldehyde;
Acetic acid;
Methyl formate;
Ethanol;
Dimethyl sulfide;
Dimethyl disulfide;
Acrylonitrile;
Acrolein;
Propanal;
Acetone;
Propionic acid;
Acetol;
Methyl acetate;
Ethyl formate;
Methyl ethyl sulfide;
Methyl ethyl disulfide;
Furan;
Thiophene;
Crotonolactone;
Pyrazine;
3-Butene nitrile;
Pyrrole;
Methyl vinyl ketone;
Diacetyl;
Butyrolactone;
Crotonic acid;
i-Butanal;
Butanal;
Butanone;
i-Butyric acid;
Acetoin;
Ethyl acetate;
Furfural;
Pyridine;
2-Pyrrolaldehyde;
2-Methylfuran;
Furfuryl alcohol;
2-Methylpyrazine;
N-Methylpyrrole;
Isoprene;
Pentadiene;
Cyclopentanone;
Pentane-2,3-dione;

2-Methyltetrahydrofuran-3-one;
Senecioic acid;
Acetylacetone;
Acetol acetate;
2-Methylbutanal;
3-Methylbutanal;
Valeraldehyde;
2-Hydroxy-3-pentanone;
3-Hydroxy-2-pentanone;
i-Valeric acid;
2-Methylbutyric acid;
Phenol;
5-Methylfurfural;
2-Acetylfuran;
Furfuryl formate;
Dimethylmaleic anhydride;
2-Methyl-3-hydroxy-γ-pyrone;
2-Acetylthiophene;
3-Methylpyridine;
2-Acetylpyrrole;
N-Methylpyrrole-2-aldehyde;
5-Methylpyrrole-2-aldehyde;
2,5-Dimethylfuran;
3-Methylcyclopentane-1,2-dione;
2,3-Dimethylpyrazine;
2,5-Dimethylpyrazine;
2,6-Dimethylpyrazine;
Furfuryl methyl sulfide;
2-Methyl-3-ethylacrolein;
1-(2'-furyl)-propane-1,2-dione;
Methyl nicotinate;
Toluene;
m-Cresol;
Guaiacol;
5-Methyl-2-acetylfuran;
Furfuryl acetate;
Methyl ethyl maleic anhydride;
2-Propionylpyrrole;
N-Methyl-2-acetylpyrrole;
N-Methyl-5-methylpyrrole-2-aldehyde;
2-Propylfuran;
3,4-Dimethylcyclopentane-1,2-dione;
3,5-Dimethylcyclopentane-1,2-dione;
3,3-Diethylcyclopentane-1,2-dione;
3-Methylcyclohexane-1,2-dione;
2,3-Dihydroxyacetophenone;
1-(2'-Furyl)-butane-1,2-dione;
1-[(5'-Methyl)-2'furyl]-propane-1,2-dione;
2-Butylfuran;
2,2'-Difurylmethane;
N-Furfuryl-2-pyrrole;
4-Vinylguaiacol; and
4-Ethylguaiacol.

(II) Insofar as cocoa flavors are concerned, aliphatic compounds such as:
Acetaldehyde;
Acetic acid;
Acetone;
Acetoxyacetone;
Acrolein;
2-Aminobutane;
n-Amyl acetate;
n-Amyl alcohol;
Amyl butyrate;
Amyl propionate;
2,3-Butaediol;
2,3-Butanedione;
2-Butanon-3-ol;
n-Butyl acetate;
n-Butyraldehyde;
n-Butyric acid;
Caproic acid;
Caprylic acid;
Citronellal;
Crotonaldehyde;
Dimethylamine;
Ethanol;
Ethyl acetate;
Ethylamine;
Ethyl caproate;
Ethyl propionate;
Formic acid;
Geraniol;
3-Heptadecanone;
1-Hexanol;
Hexyl butyrate;
Hexyl propionate;
Isoamyl acetate;
Isoamylamine;
Isobutanol;
Isobutyl acetate;
Isobutylamine;
Isobutyraldehyde;
Isovaleraldehyde;
Linalool;
Linalyl acetate;
Methanol;
Methyl acetate;
Methylamine;
α-Methylbutyric acid;
Methyl disulfide;
2-Methyl-2-hepten-6-one;
Methyl sulfide;
Methyl trisulfide;
2,4-Octadien-1-ol;
1-Octen-3-ol;
Pelargonic acid;
2,3-Pentadione;
2-Pentyl acetate;
1-Propanol;
2-Propanol;
Propionaldehyde;
Propionic acid;
1-Propyl acetate;
2-Propyl acetate;
Propyl trisulfide;
Triethylamine;
Trimethylamine;
n-Valeric acid;
Alicyclic compounds such as:
  3-Methyl-1,2-cyclopentanedione
Aromatic compounds such as:
  Acetophenone;
  Benzaldehyde;
  Benzene;
  Benzonitrile;
  Benzyl alcohol;
  Cresol;
  3,4-Dihydroxybenzoic acid;
  6,7-Dihydroxycoumarin;
  Ethyl benzoate;
  p-Ethylphenol;
  Ethyl phenylacetate;
  Eugenol;
  Guaiacol;
  o-Hydroxyacetophenone;

p-Hydroxybenzoic acid;
p-Hydroxycinnamic acid;
4-Hydroxy-3,5-dimethoxy-benzoic acid;
4-Hydroxy-3-methoxy-benzoic acid;
4-Hydroxy-3-methoxy-cinnamic acid;
o-Hydroxyphenylacetic acid;
p-Hydroxyphenylacetic acid;
p-Methoxybenzoic acid;
4-Methylguaiacol;
Methyl phenylacetate;
Phenol;
Phenyl acetate;
Phenylacetic acid;
Phenylacetic aldehyde;
2-Phenylethyl acetate;
1-Phenylethyl alcohol;
2-Phenylethyl alcohol;
2-Phenylethylamine;
2-Phenyl-2-propanol;
Toluene;
2-Methoxy-4-methylphenol;
Heterocyclic compounds such as:
  γ-Butyrolactone;
  γ-Caprolactone;
  Furan;
  Furfural;
  Furfuryl acetate;
  Furfuryl alcohol;
  2-Furyl methylacetone;
  Maltol;
  α-Methyl-γ-butyrolactone;
  2-Methylfuran;
  Methyl-5-methylfurfuryl sulfide;
  2-Methyl-3-tetrahydrofuranone;
  γ-Valerolactone;
  cis-2-Vinyl-2-methyl-5-(1-hydroxy-1-methylethyl)-tetrahydrofuran;
Pyrrole compounds such as:
  2-Acetylpyrrole;
  2-Formylpyrrole;
  1-Methyl-2-formylpyrrole;
  5-Methyl-2-formylpyrrole;
  Pyrrole;
Pyrazine compounds such as:
  2,5-Dimethyl-6-ethylpyrazine;
  2,6-Dimethyl-3-ethylpyrazine;
  2,3-Dimethylpyrazine;
  2,5-Dimethylpyrazine;
  2,6-Dimethylpyrazine;
  2-Ethyl-5-methylpyrazine;
  2-Ethyl-6-methylpyrazine;
  Methylpyrazine;
  Tetramethylpyrazine;
  Trimethylpyrazine;
  2-Ethyl-3,5,6-trimethylpyrazine;
  3-Isoamyl-2,5-dimethylpyrazine;
  5-Isoamyl-2,3-dimethylpyrazine;
  2-Isoamyl-3,5,6-trimethylpyrazine;
  Isopropyl dimethylpyrazine.
Hydrocarbons such as:
  Dimethyl naphthalene;
  Dodecane;
  Methyl diphenyl;
  Methyl naphthalene;
  Myrcene;
  Naphthalene;
  Octadecane;
  Tetradecane;
  Tetramethyl naphthalene;
  Tridecane;
  Trimethyl naphthalene;
  Undecane;
Alcohols and keto-alcohols such as:
  Acetoin;
  2-Heptanol;
  Linalool;
  1-Pentanol;
Aldehydes such as:
  Isopentanal;
  2-Methylbutanal;
Ketones such as:
  2-Heptanone;
  2-Methyl-2-hepten-6-one;
  2-Octanone;
  2-Undecanone;
Esters and lactones such as:
  Benzyl acetate;
  Ethyl caprate;
  Ethyl caproate;
  Ethyl caprylate;
  Ethyl cinnamate;
  Ethyl laurate;
  Ethyl myristate;
  Isoamyl acetate;
  γ-Nonalactone;
Acids such as:
  Isovaleric acid;
  2-Methylbutyric acid (III) Insofar as licorice flavors are concerned:
  Lavender essential oil;
  Clary sage essential oil;
  Rosemary essential oil;
  Thyme essential oil;
  Fennel essential oil;
  Mint essential oil;
  Angelica essential oil;
  Anise essential oil;
  Lemon essential oil;
  Wormwood essential oil; and
  Cinnamon essential oil.

The specific flavoring adjuvant selected for use may be either solid or liquid depending upon the desired physical form of the ultimate product, i.e., foodstuff, whether simulated or natural, and should, in any event, (i) be organoleptically compatible with the 2-acyl-5-substituted thiatetrahydrofuran-4-ones of our invention by not covering or spoiling the organoleptic properties (aroma and/or taste) thereof; (ii) be non-reactive with the 2-acyl-5-substituted thiatetrahydrofuran-4-ones of our invention and (iii) be capable of providing an environment in which the 2-acyl-5-substituted thiatetrahydrofuran-4-ones of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 2-acyl-5-substituted thiatetrahydrofuran-4-ones employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition whether foodstuff per se, chewing gum per se, medicinal product per se, toothpaste per se, or the flavoring composition itself.

The use of insufficient quantities of 2-acyl-5-substituted thiatetrahydrofuran-4-ones will, of course, substantially vitiate any possibility of obtaining the desired results while excess quantities of 2-acyl-5-substituted thiatetrahydrofuran-4-ones prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of 2-acyl-5-substituted thiatetrahydrofuran-4-ones ranging from a small but effected amount, e.g., 0.01 parts per million up to about 100 parts per million based on total composition are suitable. Concentrations in excess of the maximum quantity stated are not normally recommended, since they fail to provide commensurate enhancement or augmentation of organoleptic properties. In those instances, wherein the 2-acyl-5-substituted thiatetrahydrofuran-4-ones are added to the foodstuff as an integral component of a flavoring composition, it is, of course, essential that the total quantity of flavoring composition employed be sufficient to yield an effective 2-acyl-5-substituted thiatetrahydrofuran-4-one concentration in the foodstuff product.

Food flavoring compositions prepared in accordance with the present invention preferably contain the 2-acyl-5-substituted thiatetrahydrofuran-4-ones in concentrations ranging from about 0.05 up to about 20% by weight based on the total weight of said flavoring composition.

The compositions described herein can be prepared according to conventional techniques well known as typified by cake batters, ice creams, liquers and soft drinks and be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 2-acyl-5-substituted thiatetrahydrofuran-4-ones for example, gum arabic, gum tragacanth, carrageenan and the like, and thereafter spray-drying the resultant mixture whereby to obtain the particulate solid product. Pre-prepared flavor mixes in powder form, e.g., a cocoa-flavored powder mix and coffee-flavored powder mixes are obtained by mixing the dried solid components, e.g., starch, sugar and the like and an 2-acyl-5-substituted thiatetrahydrofuran-4-one in a dry blender until the requisite degree of uniformity is achieved.

It is presently preferred to combine with the 2-acyl-5-substituted thiatetrahydrofuran-4-ones of our invention the following adjuvants:
Diacetyl;
Benzaldehyde;
Furfural;
Furfuryl propionate;
Trimethyl pyrazine;
2,6-Dimethoxyphenol;
Pyruvic acid;
Furfuryl mercaptan; and
Furfuryl acetate.

An additional aspect of our invention provides an organoleptically improved smoking tobacco product and additives therefor, as well as methods of making the same which overcome specific desired "sweet, caramel/coffee-like, nutty and/or roasted nutty" flavor characteristics of natural tobacco are created or enhanced and may be readily controlled and maintained at the desired uniform level regardless of variations in the tobacco components of the blend.

This invention further provides improved tobacco additives and methods whereby various desirable natural aromatic tobacco flavoring characteristics with sweet, caramel/coffee, nutty and roasted nutty notes may be imparted to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient at least one 2-acyl-5-substituted thiatetrahydrofuran-4-one.

In addition to the 2-acyl-5-substituted thiatetrahydrofuran-4-ones of our invention other flavoring and aroma additives may be added to the smoking tobacco material or substituted therefor either separately or in admixture with the 2-acyl-5-substituted thiatetrahydrofuran-4-ones as follows:
  (i) Synthetic Materials:
    Beta-ethyl-cinnamaldehyde;
    Beta-cyclohomocitral;
    Eugenol;
    Dipentene;
    Damascenone;
    Damascone;
    Maltol;
    Ethyl Maltol;
    Delta-undecalactone;
    Delta-decalactone;
    Benzaldehyde;
    Amyl acetate;
    Ethyl butyrate;
    Ethyl valerate;
    Ethyl acetate;
    2-Hexenol-1;
    2-Methyl-5-isopropyl-1,3-nonadiene-8-one;
    2,6-Dimethyl-2,6-undecadiene-10-one;
    2-Methyl-5-isopropyl acetophenone;
    2-Hydroxy-2,5,5,8a-tetramethyl-1-(2-hydroxyethyl)-decahydronaphthalene;
  Dodecahydro-3a,6,6,9a-tetramethylnaphtho-[2,1,b]-furan;
  4-Hydroxy hexanoic acid, gamma lactone; and
  Polyisoprenoid hydrocarbons defined in Example V of U.S. Pat. No. 3,589,372 issued on June 29, 1971.

(ii) Natural Oils:
Celery seed oil;
Coffee extract;
Bergamot oil;
Cocoa extract;
Nutmeg oil; and
Origanum oil.

An aroma and flavoring concentrate containing a 2-acyl-5-substituted thiatetrahydrofuran-4-one and, if desired, one or more of the above-indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet, coffee/caramel, nutty or roasted nutty notes, we have found that satisfactory notes are obtained if the proportion by weight of the sum total of 2-acyl-5-substituted thiatetrahydrofuran-4-ones to smoking tobacco material is between 10 ppm and 1,500 ppm (0.001–0.15%) of the active ingredients to the smoking tobacco material. We have further found that satisfactory results are obtained if the proportion by weight of the sum total of 2-acyl-5-substituted thiatetrahydrofuran-4-ones used to flavoring material is between 2,500 and 15,000 ppm (0.25–1.5%).

Any convenient method for incorporating the 2-acyl-5-substituted thiatetrahydrofuran-4-ones into the tobacco product may be employed. Thus, the 2-acyl-5-substituted thiatetrahydrofuran-4-ones taken alone or along with other flavoring additives may be dissolved in a suitable solvent such as ethanol, diethyl ether, tetrahydrofuran and/or volatile organic solvents and the resulting solution may either be sprayed on the cured, cased and blended tobacco material or the tobacco material may be dipped into such solution. Under certain circumstances, a solution of the 2-acyl-5-substituted thiatetrahydrofuran-4-ones taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the 2-acyl-5-substituted thiatetrahydrofuran-4-ones in excess of the amounts of concentrations above-indicated so that when blended with other tobaccos, the final product will have the percentage within the indicated range.

In accordance with one specific example of our invention, an aged, cured and shredded domestic burley tobacco is sprayed with a 20% ethyl alcohol solution of 5-acetyl-2(2-methyl-3-furylthio)-dihydro-2,5-dimethyl-3,2H-furanone (mixture of "cis" and "trans" isomers produced according to Example I, infra) in an amount to provide a tobacco composition containing 50 ppm by weight of 5-acetyl-2(2-methyl-3-furylthio)-dihydro-2,5-dimethyl-3,2H-furanone on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweeter, more aromatic and having sweet, caramel/coffee-like, nutty/pyrazine-like and roasted nutty-like aromas and tastes.

While our invention is particularly useful in the manufacture of smoking tobacco, such as cigarette tobacco, cigar tobacco and pipe tobacco, other tobacco products formed from sheeted tobacco dust or fines may also be used. Likewise the 2-acyl-5-substituted thiatetrahydrofuran-4-ones of our invention can be incorporated with materials such as filter tip materials, seam paste, packaging materials and the like which are used along with tobacco to form a product adapted for smoking. Furthermore, the 2-acyl-5-substituted thiatetrahydrofuran-4-ones can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The following Examples serve to illustrate techniques for practicing our invention. It will be understood that these Examples are illustrative and that the invention is to be considered restricted thereto only as indicated in the appended claims.

All parts and percentages given herein are by weight unless otherwise specified.

EXAMPLE I

Preparation of 5-Acetyl-2(2-methyl-3-furylthio)-dihydro-2,5-dimethyl-3,2H-furanone According to the Reaction of 2-Methyl-3-furanthiol with the Diacetyl Dimer Reaction:

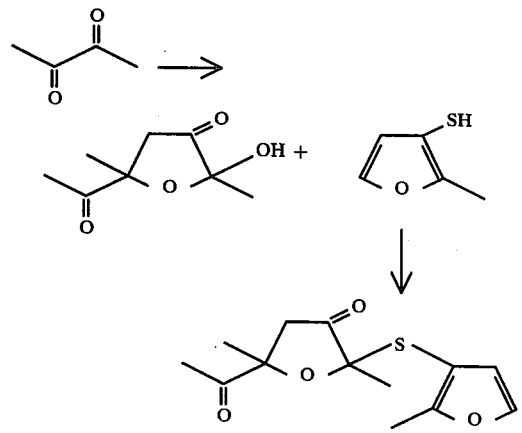

Into a 5 liter reactor equipped with reflux condenser, stirrer and cooling bath is added the following ingredients:

Diacetyl — 320 grams
Water — 3,200 ml

The reaction mass is cooled to 3° C at which point a solution of 54.4 grams of potassium hydroxide and 1,600 ml of water is added over a period of 20 minutes. 85 Grams of 50% sulfuric acid is then added to the reaction mixture bringing the pH to 5.

The reaction mass is then saturated with 1600 grams of sodium chloride and then extracted with four 200 ml portions of methylene dichloride. The reaction mass is then dried over anhydrous sodium sulphate and stripped of solvent. The resulting product is then distilled through a 6-inch Vigreaux column followed by redistillation yielding the diacetyl dimer.

Into a 250 ml reaction flask equipped with reflux condenser, stirrer, thermometer and heating mantle is placed 20 grams (17.7 ml) of 2-methyl-3-furanthiol. 10 ml tetrahydrofuran and 0.5 ml concentrated HCl is then added. The reaction mass is heated to 50° C and, over a 10 minute period, 30 grams of diacetyl dimer prepared as above in 20 grams of tetrahydrofuran is added. 20 ml tetrahydrofuran additional used to rinse the addition flask is then added.

The reaction mass is then stirred for 5 hours at 50° C with GC samples taken each hour.

The reaction mass is stirred for 5 hours and then 20 ml saturated sodium bicarbonate is added. The resulting mixture is transferred to a separatory funnel containing 200 ml of water and in the separatory funnel the oil phase is separated from the aqueous phase. The aqueous phase is extracted with one portion (30 ml) of methylene dichloride and the extract is combined with the oil layer. The resulting material is dried over anhydrous sodium sulphate and filtered and then stripped at atmospheric pressure to 80° C. The resulting product is then distilled through a micro Vigreaux column.

The resulting compound is confirmed by IR, GLC, NMR and Mass Spectral analyses to be two isomers having the structures:

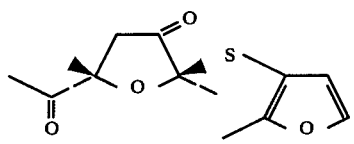

and

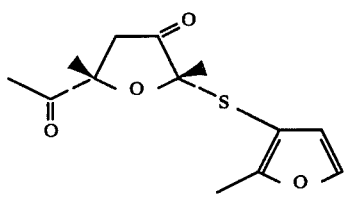

What is claimed is:

1. A genus of 2-acyl-5-substituted thiatetrahydrofuran-4-one compounds selected from the group of compounds having the structures:

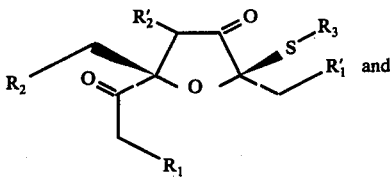

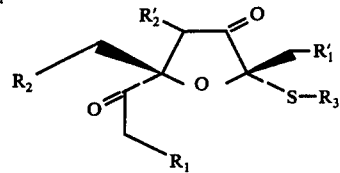

wherein $R_1$, $R_2$, $R_1'$ and $R_2'$ are the same or different and each is selected from the group consisting of hydrogen and methyl and $R_3$ is selected from the group consisting of $C_1$-$C_9$ alkyl; benzyl; phenyl; substituted or unsubstituted allyl having the structure:

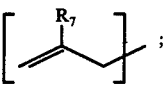

3-furyl substituted or unsubstituted having the structure:

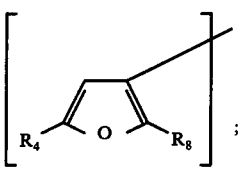

oxy or hydroxy alkyl having the structure:

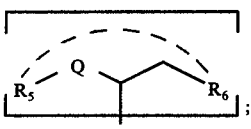

wherein Q is:

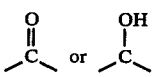

and $R_5$ and $R_6$ are the same or different lower alkyl taken separately or, taken together, $R_5$ and $R_6$ complete a cyclialkyl ring; and wherein each of $R_4$, $R_7$ and $R_8$ are the same or different and are hydrogen or methyl.

2. A compound defined according to claim 1 wherein $R_1$, $R_2$, $R_1'$ and $R_2'$ are each hydrogen and $R_3$ is 2-methyl-3-furyl.

* * * * *